(12) United States Patent
Anderson et al.

(10) Patent No.: US 11,185,637 B2
(45) Date of Patent: Nov. 30, 2021

(54) MIXING SYRINGE ASSEMBLY

(71) Applicant: CONSORT MEDICAL PLC, Hemel Hempstead (GB)

(72) Inventors: Ian Anderson, Newmarket (GB); Matt Ekman, Macclesfield (GB); Robert Glover, Sheffield (GB); Rachel Koppelman, Cambridge (GB)

(73) Assignee: CONSORT MEDICAL PLC, Hempstead (GB)

( * ) Notice: Subject to any disclaimer, the term of this patent is extended or adjusted under 35 U.S.C. 154(b) by 65 days.

(21) Appl. No.: 14/777,885

(22) PCT Filed: Mar. 26, 2014

(86) PCT No.: PCT/GB2014/050965
§ 371 (c)(1),
(2) Date: Sep. 17, 2015

(87) PCT Pub. No.: WO2014/155114
PCT Pub. Date: Oct. 2, 2014

(65) Prior Publication Data
US 2016/0279341 A1   Sep. 29, 2016

(30) Foreign Application Priority Data

Mar. 26, 2013 (GB) .................................... 1305489

(51) Int. Cl.
*A61M 5/315* (2006.01)
*A61M 5/31* (2006.01)

(52) U.S. Cl.
CPC ...... *A61M 5/31596* (2013.01); *A61M 5/3137* (2013.01); *A61M 5/31505* (2013.01)

(58) Field of Classification Search
CPC ............ A61M 5/31596; A61M 5/3137; A61M 5/31505; A61M 2005/31598;
(Continued)

(56) References Cited

U.S. PATENT DOCUMENTS 3,659,749 A * 5/1972 Schwartz .......... A61M 5/31596
222/129
3,766,917 A  10/1973 Wimmer
(Continued)

FOREIGN PATENT DOCUMENTS

CH      445 721 A    10/1967
DE     1291859 B      4/1969
(Continued)

OTHER PUBLICATIONS

International Preliminary Report on Patentability for PCT/GB2014/050965 dated May 30, 2014 (8 pages).
(Continued)

*Primary Examiner* — Brandy S Lee
*Assistant Examiner* — Hong-Van N Trinh
(74) *Attorney, Agent, or Firm* — Taft Stettinius & Hollister LLP; Ryan O. White; Derek B. Lavender (57) ABSTRACT

A syringe assembly comprising a barrel for containing one or more medicaments, the barrel having a front outlet for allowing the expulsion of said one or more medicaments from the said barrel through said outlet, and a first stopper disposed in the barrel and axially moveable therein and defining a first volume in the barrel axially forwards of the first stopper and a second volume in the barrel axially rearwards of the first stopper. The first stopper has a two way valve that is moveable between a sealing configuration and an open configuration to selectively put the first volume in fluid communication with the second volume. The two way valve is moveable from the sealing configuration to the open configuration by an increase in fluid pressure in either of the first and second volumes. The syringe assembly additionally comprises a second stopper disposed in the barrel axially rearward of the first stopper and axially moveable therein, the second stopper providing a fluid tight seal at a rear end
(Continued)

of the second volume. The syringe assembly further comprises a first plunger rod connected to the first stopper and extending axially rearwardly through the second stopper, the second stopper sealingly engaging with the first plunger rod but permitting axial sliding of the first plunger rod therethrough. The first plunger rod is axially moveable so as to axially move the first stopper and pressurise either of the first volume and second volume causing the two way valve to move into the open configuration and fluidly connect the first volume and second volume.

14 Claims, 7 Drawing Sheets

(58) Field of Classification Search
CPC .... A61M 5/31515; A61M 2005/31508; A61M 5/31576; A61M 2039/2433; A61M 2039/244; A61M 2039/2446; A61M 2039/246; A61M 3/005; A61M 2005/2451; A61M 5/284; A61M 5/2448; A61M 5/31511; A61M 5/19; A61M 5/24; A61M 5/3294; A61M 2005/3128
USPC ....... 604/82, 89, 90; 215/355, 220, 231, 260
See application file for complete search history.

(56) References Cited

U.S. PATENT DOCUMENTS

| | | | | |
|---|---|---|---|---|
| 4,437,858 A | * | 3/1984 | Ty | A61M 5/284 604/90 |
| 5,453,093 A | * | 9/1995 | Haining | A61M 5/31511 604/110 |
| 5,605,542 A | * | 2/1997 | Tanaka | A61M 5/284 604/86 |
| 5,630,800 A | * | 5/1997 | Blank | A61M 5/31596 604/228 |
| 5,925,019 A | | 7/1999 | Ljungquist | |
| 6,319,234 B1 | * | 11/2001 | Restelli | A61M 5/326 604/110 |
| 6,488,651 B1 | | 12/2002 | Morris et al. | |
| 2003/0040701 A1 | * | 2/2003 | Dalmose | A61M 5/31596 604/87 |
| 2006/0100587 A1 | | 5/2006 | Bertron et al. | |
| 2013/0096493 A1 | * | 4/2013 | Kubo | A61M 3/0262 604/58 |

FOREIGN PATENT DOCUMENTS

| | | | | |
|---|---|---|---|---|
| EP | 0242956 A1 | * | 10/1987 | ........ A61M 5/31596 |
| EP | 1520597 A1 | | 4/2005 | |
| GB | 1214053 A | | 12/1970 | |
| JP | 5888234 B2 | * | 3/2016 | .......... A61M 3/0262 |
| SE | WO 2011139198 A1 | * | 11/2011 | ........ A61M 5/31596 |
| WO | WO 94/09839 A1 | | 5/1994 | |
| WO | WO 98/01174 A1 | | 1/1998 | |
| WO | WO-9801174 A1 | * | 1/1998 | ........ A61M 5/31596 |
| WO | 2005065752 A1 | | 7/2005 | |
| WO | WO 2006/003653 A2 | | 1/2006 | |
| WO | WO 2008/150208 A1 | | 12/2008 | |
| WO | WO 2011/139198 A1 | | 11/2011 | |

OTHER PUBLICATIONS

International Search Report and Written Opinion for PCT/GB2014/050965 dated May 30, 2014 (12 pages).
Combined Search and Examination Report under Sections 17 and 18(3) for UK Application No. GB1305489.5 dated Mar. 26, 2015 (6 pages).
Japanes Office Action and translation; dated Jan. 30, 2018; 7 pages.
Russian Office Action and Translation; dated Feb. 15, 2018; 13 pages.
Chilean Office Action; dated Nov. 16, 2017; 9 pages.

* cited by examiner

MIXING SYRINGE ASSEMBLY

This application is a U.S. national stage application under 35 U.S.C. § 371 of PCT International Application Serial No. PCT/GB2014/050965, which has an international filing date of Mar. 26, 2014 designates the United States of America, and claims the benefit of GB Application No. 1305489.5, which was filed on Mar. 26, 2013. The disclosures of each of these prior applications are hereby expressly incorporated by reference in their entirety.

This invention relates to a syringe assembly, and more particularly, to a valved mixing syringe assembly suitable for mixing two or more medicaments prior to delivery.

BACKGROUND

It is known to provide a syringe having two or more chambers containing different medicaments that are separated within the syringe. Such devices may be used to mix the two or more medicaments shortly before delivery which may be necessary if the two or more medicaments are unstable over longer periods of time when in a mixed state (e.g. in storage). Mixing syringes often include a mechanism for putting the two or more medicament chambers in fluid communication with one another at a desired time.

An example of a two-chamber injector is described in WO-A-97/09839 (STI International Limited). The injector includes two chambers that are separated by a flexible wall member. A forward one of the chambers contains a dry ingredient and a rearward one of the chambers contains a liquid ingredient. The flexible wall member is shaped such that, when it is moved axially rearwardly within the device, its movement through the liquid in the rear chamber causes the flexible wall member to flex slightly. This flexion allows the liquid ingredient to bypass or escape around the exterior periphery of the flexible wall member and into the forward chamber containing the dry ingredient.

In at least one embodiment, it is an object of the present invention to provide an alternative syringe assembly that permits the mixing of two or more ingredients, where, preferably, at least one of the ingredients is of a viscous nature.

BRIEF SUMMARY OF THE DISCLOSURE

In accordance with a first aspect of the present invention there is provided a syringe assembly comprising:
 a barrel for containing one or more medicaments, the barrel having a front outlet for allowing the expulsion of said one or more medicaments from the said barrel through said outlet;
 a first stopper disposed in the barrel and axially moveable therein and defining a first volume in the barrel axially forwards of the first stopper and a second volume in the barrel axially rearwards of the first stopper, the first stopper having a two way valve that is moveable between a sealing configuration and an open configuration to selectively put the first volume in fluid communication with the second volume, the two way valve being moveable from the sealing configuration to the open configuration by an increase in fluid pressure in either of the first and second volumes;
 a second stopper disposed in the barrel axially rearward of the first stopper and axially moveable therein, the second stopper providing a fluid tight seal at a rear end of the second volume; and
 a first plunger rod connected to the first stopper and extending axially rearwardly through the second stopper, the second stopper sealingly engaging with the first plunger rod but permitting axial sliding of the first plunger rod therethrough;
 wherein the first plunger rod is axially moveable so as to axially move the first stopper and pressurise either of the first volume and second volume causing the two way valve to move into the open configuration and fluidly connect the first volume and second volume.

The syringe assembly of the first aspect of the present invention allows fluid communication between the first and second chambers in response to an increase in pressure in either of the first and second chambers. The two way valve is normally in a sealing (closed) configuration when no or insufficient pressure forces are acting on it. Upon an increase in fluid pressure in either of the first and second volumes, the two way valve is moveable from the sealing configuration to the open configuration. In practice, this means that the first stopper may be moved axially forwardly and axially rearwardly in succession, by axial translation of the first plunger rod, in order to open the two way valve and effectively mix medicaments initially stored in the first and second volumes. This arrangement is particularly suitable for the efficient and effective mixing of two medicaments where one or both of the two medicaments is/are particularly viscous. Known prior art arrangements do not permit fluid communication between two adjacent chambers in response to an increase in pressure in either chamber. As a result, known prior art arrangements do not permit the successive forward and rearward movement of the stopper to facilitate effective mixing of ingredients contained in the two chambers.

In one preferable embodiment, the syringe assembly further comprises a removeable transit clip that is configured to prevent axial movement of the first plunger rod.

The first plunger rod may include one or more finger loops for facilitating handling of the first plunger rod.

The syringe assembly may further comprise a second plunger rod connected to the second stopper, wherein axial movement of the second plunger rod causes axial movement of the second stopper. Optionally, the syringe assembly further comprises an engagement mechanism for engaging the first plunger rod with the second plunger rod in a predetermined position of the first plunger rod relative to the second plunger rod. The engagement mechanism may include engagement members connected to the first plunger rod, the engagement members being arranged to engage with the second plunger rod when the first plunger rod is at a predetermined axial position and/or rotational position relative to the second plunger rod. The engagement members may project radially inwardly from a sleeve connected to the first plunger rod and surrounding the second plunger rod. The engagement members may be arranged to engage with a rear end of the second plunger rod by abutting said rear end of said second plunger rod.

The syringe assembly may further comprise a locking mechanism for limiting axial movement of the second plunger rod. Axial movement of the second plunger rod may only be permitted when the second plunger rod is in a predetermined rotational position. The locking mechanism may comprise a collar and axial movement of the second plunger rod is permitted when the second plunger rod is in a predetermined rotational position relative to the collar and axial abutment between the collar and the second plunger rod prevent relative axial movement in rotational positions other than the predetermined rotational position.

The two way valve may comprise a resilient seal that deforms under a predetermined fluid pressure, wherein the resilient seal may include a plurality of flexible flaps. The resilient seal may extend along an arc around the first stopper, wherein the angular extent of the arc is less than 360°.

The first stopper may include the resilient seal and further include a permanent seal about an outer circumference of the first stopper that is axially spaced from the resilient seal, and a by-pass channel providing a fluidic passageway from between the resilient seal and the permanent seal around the permanent seal.

The fluid tight seal provided by the second stopper may be a sterile seal and/or a microbiological seal.

BRIEF DESCRIPTION OF THE DRAWINGS

Embodiments of the invention are further described hereinafter with reference to the accompanying drawings, in which:

FIG. 1A shows the syringe assembly prior to use, FIGS. 1B and 1C show the syringe assembly during mixing, and FIG. 1D shows the syringe assembly during delivery;

FIGS. 2A to 2E are cross sectional views of a syringe assembly in accordance with an alternative embodiment of the present invention, where FIG. 2A shows the syringe assembly prior to use, FIGS. 2B and 2C show the syringe assembly during mixing, FIG. 2D shows the syringe assembly after mixing and prior to delivery, and FIG. 2E shows the syringe assembly during delivery;

DETAILED DESCRIPTION

Figure 1A:
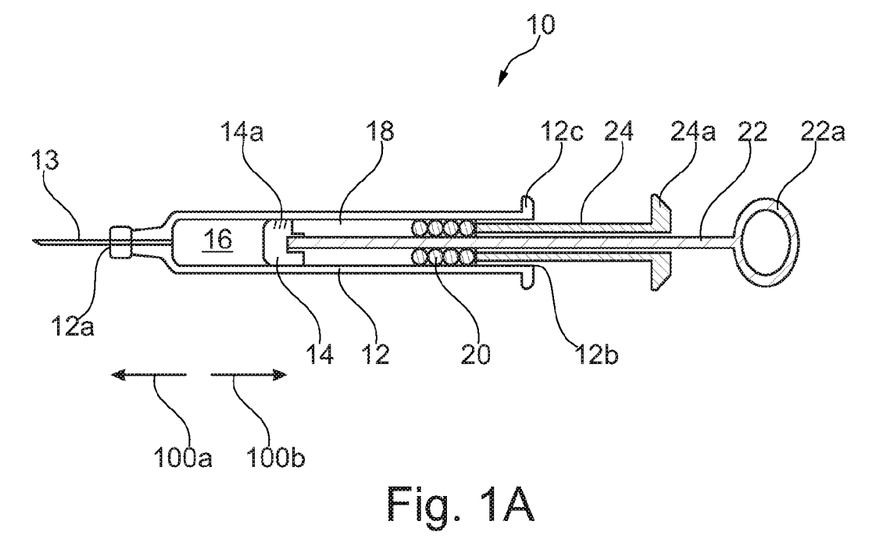
FIGS. 1A to 1D are cross sectional views of a syringe assembly in accordance with an embodiment of the present invention, where

FIGS. 1A to 1D are cross sectional views of a syringe assembly 10 in accordance with an embodiment of the present invention. FIG. 1A shows the syringe assembly 10 prior to use. The syringe assembly 10 includes a barrel 12 for containing medicaments and has a front outlet 12a for allowing the expulsion of medicament. In the embodiment shown in FIGS. 1A to 1D, the front outlet 12a is provided with a needle 13 for penetrating an injection site and delivering medicament from the barrel 12 thereto. The barrel 12 has an open rear end 12b and a radially extending flange 12c which may facilitate manual handling of the syringe assembly 10. The syringe assembly 10 generally extends along an axial dimension which will be referenced hereinafter to aid the description of the syringe assembly 10 and its components. In particular, a forward axial direction 100a points along the length of the syringe assembly 10 towards the forward end where medicament will be expelled (i.e. towards the injection site), whereas a rearward axial direction 100b points in the opposite direction, as indicated in FIG. 1A. All references herein to forwards and backwards are intended to mean axially forwards and axially rearwards, respectively, unless otherwise stated.

A first stopper 14 is disposed in the barrel 12 and is axially moveable therein. The first stopper 14 defines a first volume 16 in the barrel 12, which is axially forward of the first stopper 14, and defines a second volume 18 in the barrel 12, which is axially rearward of the first stopper 14. The first and second volumes 16, 18 are each suitable for containing fluidic medicaments which may be different to one another.

A second stopper 20 is disposed in the barrel 12 axially rearward of the first stopper 14 and defines the axially rearward limit of the second volume 18 (the front of the barrel 12 defining the axially forward limit of the first volume 16). Like the first stopper 14, the second stopper 20 is axially moveable within the barrel 12. The second stopper 20 provides a fluid tight seal at the rear of the second volume 18 such that no fluid from the second volume 18 can exit the open rear end 12b of the barrel 12.

The first stopper 14 has a first plunger rod 22 connected thereto that extends axially rearwardly through the second stopper 20. The second stopper 20 sealingly engages the first plunger rod so as to seal the rear of the second volume 18 but permits axial sliding of the first plunger rod 22 through the second stopper 20. Therefore, the second stopper 20 seals an annulus around between the outside of the first plunger rod 22 and the inside surface of the barrel 12. The first plunger rod 22 includes a finger loop 22a for facilitating handling of the first plunger rod 22. Axial movement of the first plunger rod 22 results in axial movement of the first stopper 14 within the barrel 12. In alternative embodiments, there may be no finger loop 22a provided, or an alternative formation that facilitates handling of the first plunger rod 22.

In the embodiment shown in FIGS. 1A to 1D, the second stopper 20 is provided with a second plunger rod 24 that extends axially rearwardly from the second stopper 20 radially outward of the first plunger rod 22. Axial movement of the second plunger rod 24 results in axial movement of the second stopper 20 within the barrel 12. The first plunger rod 22 is axially longer than the second plunger rod 24 such that at least the rear end of the first plunger rod (which includes the finger loop 22a) is always exposed rearward of the second plunger rod 24 regardless of the relative positions of the first plunger rod 24 and second plunger rod 22.

The first stopper 14 includes a two way valve portion 14a that is moveable between a sealing configuration and an open configuration. In the sealing configuration, the first volume 16 is fluidically sealed from the second volume 18, whereas in the open configuration, the first volume 16 is fluidly connected to the second volume 18. The two way valve portion 14a is moveable from the sealing configuration to the open configuration by an increase in pressure either axially forwards or axially rearwards of the first stopper 14. When disposed in the barrel 12 as shown in FIG. 1A, the first volume 16 is axially forwards of the first stopper 16 and the second volume 18 is axially rearwards of the first stopper 14 so an increase of pressure in either of the first volume 16 or second volume 18 may cause the two way valve portion 14a to move from the sealing configuration to the open configuration. Crucially, the two way valve portion 14a is moveable from the sealing configuration to the open configuration by an increase in pressure both axially forwardly and axially rearwardly such that, if fluid is present in the first and second volumes 16, 18, axial movement of the first stopper 14 in either the axially forward or axially rearward direction will cause an increase in fluid pressure in one of the first and second volumes 16, 18 (depending on the direction of movement) which will subsequently cause the two way valve portion 14a to open and fluidly connect the first and second volumes 16, 18. The two way valve portion 14a will move back to the sealing configuration when the axially forward and axially rearward forces acting on it equalize (e.g. if the first stopper 14 is stationary in the barrel 12 for a period of time).

The operation of the syringe assembly 10 will now be described with reference to FIGS. 1B to 1D. To initiate mixing of medicaments contained in the first and second volumes 16, 18, the first stopper 14 is moved axially forwardly and axially rearwardly in the barrel 12 successively while the second stopper 20 remains stationary within the barrel 12. To do this, the first plunger rod 22 is moved axially forwardly and axially rearwardly relative to the barrel 12 whilst the second plunger rod 24 is not moved relative to the barrel 12.

Figure 1B:
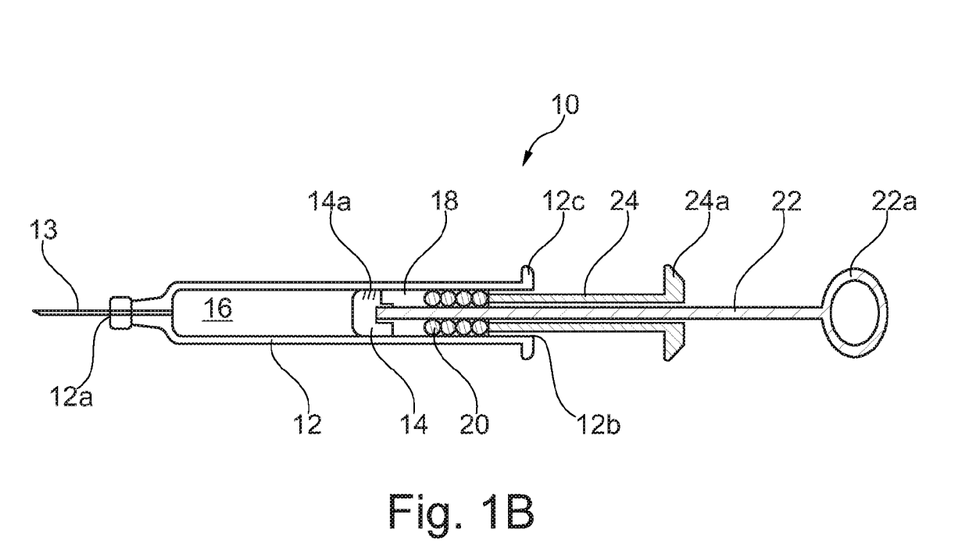
Figure 1C:
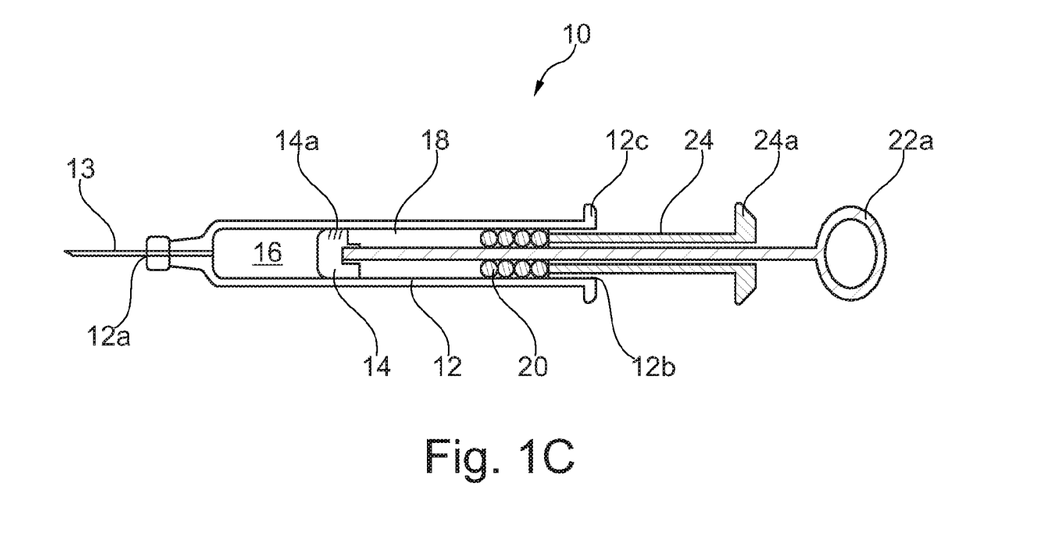
Figure 1D:
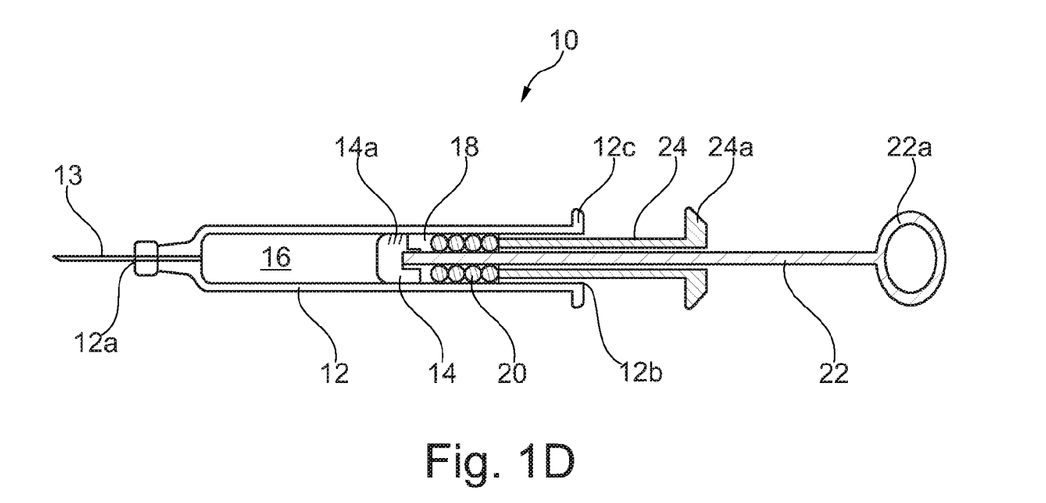

FIG. 1B shows the first stopper 14 and first plunger rod 22 moved axially rearwardly compared to the configuration shown in FIG. 1A. In moving to the configuration shown in FIG. 1B, the fluid in the second volume 18 would have increased in pressure to a point where the increase causes the two way valve portion 14a to move into the open configuration and fluidly connect the second volume 18 with the first volume 16. Due to the higher pressure in the second volume 18, the fluid in the second volume 18 passes through the open two way valve portion 14a into the first volume 16. This flow of fluid permits the rearward axial movement of the first stopper 14 resulting in the reduction of the second volume 18 and the increase of the first volume 16. Once all of the fluid has been allowed to enter a common volume (e.g. the first volume 16), the first stopper 14 may be moved axially forwards once more by translating the first plunger rod 22 to encourage mixing of the previously separate fluids, as shown in FIG. 1C. Indeed, the first stopper 14 may be moved successively axially forwardly and axially rearwardly within the barrel 12 to encourage thorough mixing of the two fluids. Such thorough mixing may be required when one or both of the two fluids is/are particularly viscous or immiscible. In the absence of this agitation, the two fluids may remain unmixed despite residing in the same volume 16, 18. Nevertheless, in certain embodiments, a single rearward movement of the first stopper 14 may be sufficient for adequate mixing such that subsequent successive forward and rearward movements are not necessary. It is noted that for certain drugs, the agitation of the drug caused by successive forward and rearward movements may be detrimental and so may preferably be limited.

Once the two fluids have been completely mixed, the first stopper 14 is moved axially rearwardly (by pulling the first plunger rod 22 axially rearwardly) to meet with the second stopper 20 thus reducing the second volume 18 to substantially zero so that substantially all of the mixed fluid is in the (now larger) first volume 16. To dispense the mixed fluid from the first volume, the second stopper 20 is moved axially forwardly (by moving the second plunger rod 24 axially forwardly). This action causes both of the first stopper 14 and second stopper 20 to move axially forwardly within the barrel 12 and pressurize the mixed fluid thus causing the mixed fluid to exit the barrel 12 via the front outlet 12a and needle 13.

An alternative syringe assembly 10' in accordance with an embodiment of the present invention is shown in FIGS. 2A to 2E. The syringe assembly 10' of FIGS. 2A to 2E shares many common features with the syringe assembly described above in relation to FIGS. 1A to 1D. New or modified features in FIGS. 2A to 2E are denoted with a new or primed (') reference numeral. The syringe assembly 10' of FIGS. 2A to 2E operates to mix two fluids in the first and second volumes 16, 18, just as the syringe assembly of FIGS. 1A to 1D does.

The syringe assembly 10' shown in FIGS. 2A to 2E has a radially extending flange 12c' that is larger than that of the syringe assembly 10 of FIGS. 1A to 1D. Either embodiment 10, 10' may include a radially extending flange of any size, however. A larger radially extending flange 12c' may facilitate easier handling of the syringe assembly 10, 10'.

The syringe assembly 10' includes a removable transit clip 15 (which may be present in any embodiment in accordance with the present invention, including the embodiment 10 described above) that, when assembled on the syringe assembly 10' prevents axial movement of the first plunger rod 22 so as to prevent accidental mixing between the first and second volumes 16, 18, for example, when the syringe assembly is being transported and handled prior to use. The transit clip 15 may be any removable abutment or gripping mechanism that prevents axial movement of the first plunger rod 22 relative to the barrel 12. The transit clip 15 may additionally prevent axial movement of the second plunger rod 24 by abutment or gripping. In alternative embodiments, a part of an outer packaging or other component may abut, interfere or grip the first plunger rod 22 and/or second plunger rod 24 so as to prevent respective axial movement thereof prior to use. When it is intended to use the assembly 10' to administer the medicament, the outer packaging (or other component) may be removed so as to permit axial movement of the first plunger rod 22 and/or second plunger rod 24.

The first plunger rod 22 includes a (double) finger loop 22a' for facilitating handling of the first plunger rod 22. In the embodiment shown in FIGS. 2A to 2E, the first plunger rod 22 is rotatable about a longitudinal axis of the syringe assembly 10' (i.e. a central axis of the syringe assembly 10' that is parallel to the axial directions 100a, 100b) relative to the second plunger rod 24 and barrel 12. FIG. 3 shows a rear end view from line A-A in FIG. 2A where the syringe assembly 10' is in a first configuration. As shown in FIG. 3, the finger loop 22a' is orientated perpendicularly to the flange 12c' of the barrel 12.

Figure 2A:
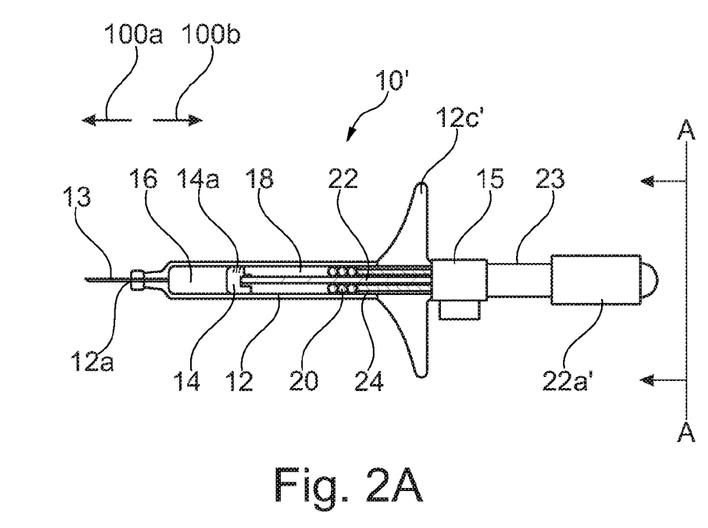
Figure 2B:
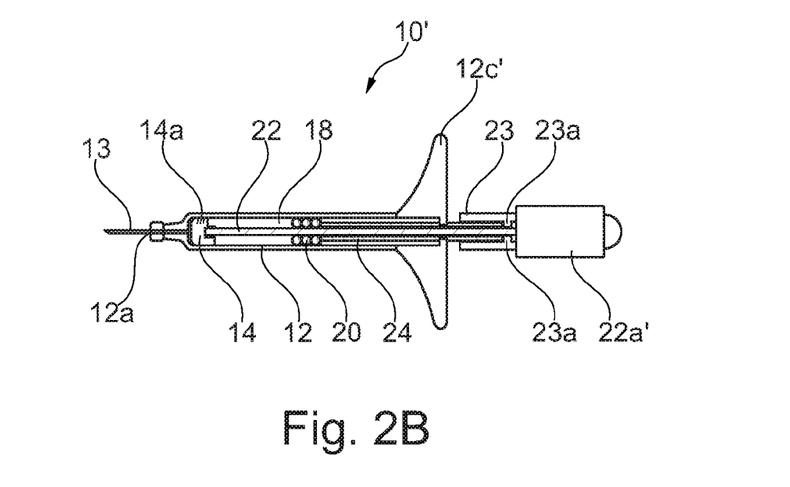
Figure 3:
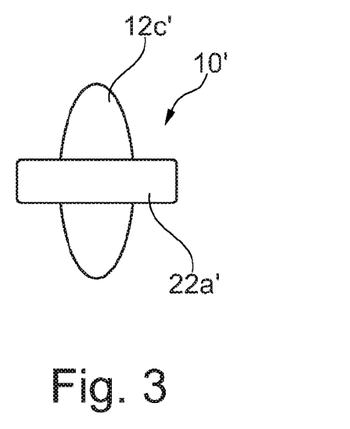
FIG. 3 shows a rear end view of the syringe assembly shown in FIG. 2A.
Figure 4:
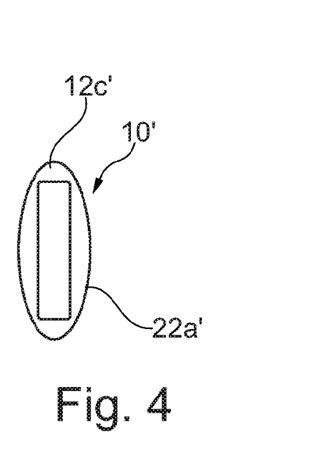
FIG. 4 shows a rear end view of the syringe assembly shown in FIG. 2D.

In order to initiate mixing in the syringe assembly 10', the transit clip 15 must first be removed (in the specific embodiment shown in FIG. 2A). Once removed, the first plunger rod 22 may be moved axially forward and rearward to mix the fluids in the first and second volumes 16, 18 (via the open two way valve portion 14a). FIG. 2B shows the syringe assembly 10' during the mixing stage with the first stopper 14 at a forward end of the barrel. In FIG. 2B it can be seen that the first plunger rod 22 includes an engagement mechanism that comprises a sleeve 23 extending axially forwardly from the finger loop 22a'. The sleeve 23 is of a diameter that is larger than the diameter of the second plunger rod 24 so as to surround the second plunger rod 24. The sleeve 23 has a rear set of engagement members 23a that project radially inwardly and to abut a rear end of the second plunger rod 24 to limit the forwardmost position of the first plunger rod 22 relative to the second plunger rod 24. Incidentally, in the embodiment shown in FIG. 2B, the first stopper 14 is also at its forwardmost position in the barrel 12 when the rear engagement elements 23a abut the second plunger rod 24. Therefore the front of the barrel 12 may limit the forwardmost axial position of the first plunger rod 22 in place of or in addition to the rear engagement elements 23a.

Figure 2C:
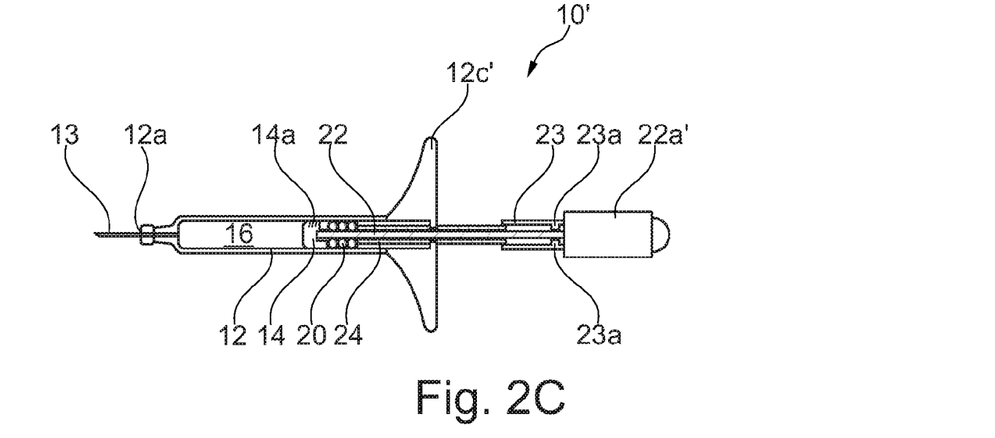
Figure 2D:
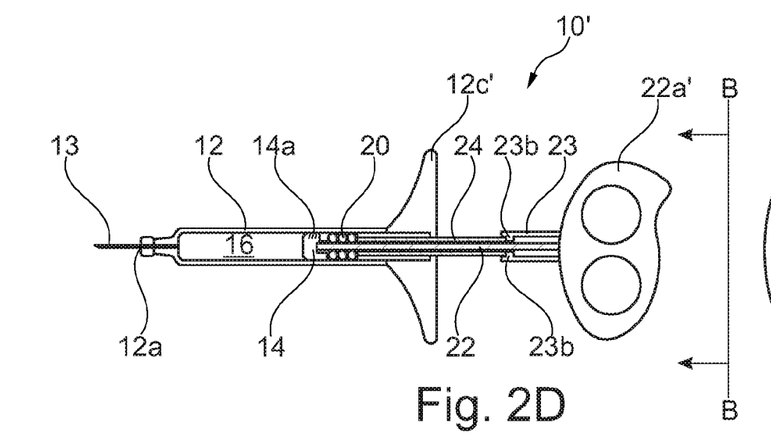

When the fluids in the first volume 16 and second volume 18 have been entirely mixed, the first plunger rod 22 is moved axially rearwardly to move the first stopper 14 axially rearwardly until the first stopper 14 meets the second stopper 20, reducing the second volume 18 to substantially zero and forcing all of the mixed fluids into the (now enlarged) first volume 16. FIG. 2C shows the syringe assembly 10' with the first stopper 14 withdrawn axially rearwardly so that it is in contact with the second stopper 20.

Figure 2E:
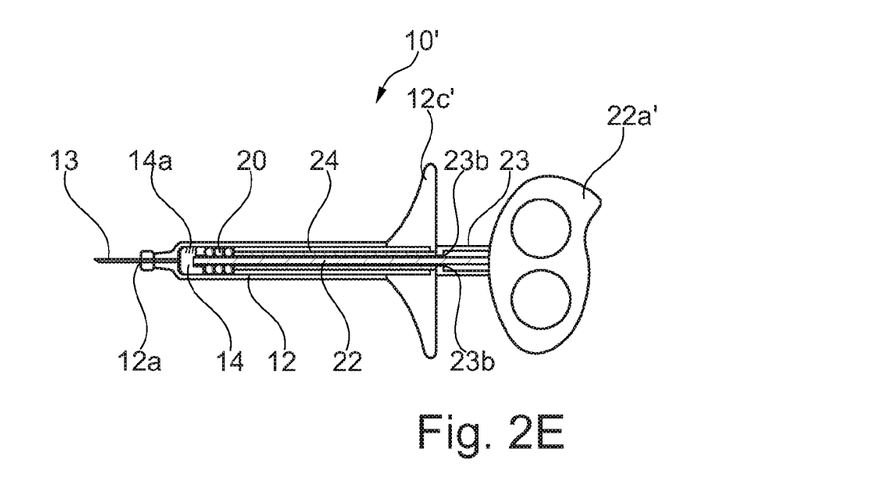

Unlike the second plunger rod 24 of the embodiment described above in relation to FIGS. 1A to 1D, the second plunger rod 24 of the embodiment of FIGS. 2A to 2E does not have a flange (24a). Therefore, in order to move the second plunger rod 24 axially forwardly to deliver a dose of (mixed) medicament, the first plunger rod 22 must engage with the second plunger rod 24. In order to permit the required engagement, the finger loop 22a' of the first plunger rod 22 is rotated about the longitudinal axis by 90° so as to be aligned with the flange 12c' of the barrel 12. In doing so, front engagement members 23b are brought into alignment with the rear end of the second plunger rod 24 such that axially forward movement of the first plunger rod 22 relative to the second plunger rod 24 is not permitted due to abutment between the front engagement members 23b and the rear end of the second plunger rod 24. Prior to the above-described alignment, the front engagement members 23b are able to travel axially along grooves or channels in the second plunger rod 24. Thus, axially forward movement of the first plunger rod 22 causes axially forward movement of the second plunger rod 24 also, and causes the content of the first volume 16 to be pressurized resulting in the expulsion of the contents through the needle 13. FIG. 2E shows the syringe assembly 10' at the end of delivery when the entire contents of the barrel 12 have been dispensed.

Although the sleeve 23 and front and rear engagement elements 23b, 23a represent an exemplary embodiment of a suitable engagement means for selectively engaging the first plunger rod 22 with the second plunger rod 24, any other suitable mechanism may be employed within the scope of the present invention. Mechanisms using abutment or gripping means are particularly suitable, and mechanisms requiring rotation to engage/disengage the first and second plunger rods 22, 24 are particularly preferable as they reduce the risk of accidental engagement and provide a clear indicator to the user as to whether the first and second plunger rods 22, 24 are engaged or not. Indeed, a 90° rotation is one preferable choice. Whilst the above-described embodiment requires a 90° turn of the first plunger rod 22 for it to engage with the second plunger rod 24, other angles may be employed in alternative embodiments in accordance with the present invention. In preferable embodiments, the first plunger rod 22 will be at a predetermined axial position relative to the second plunger rod 24 before such a rotation is permitted.

Figure 5:
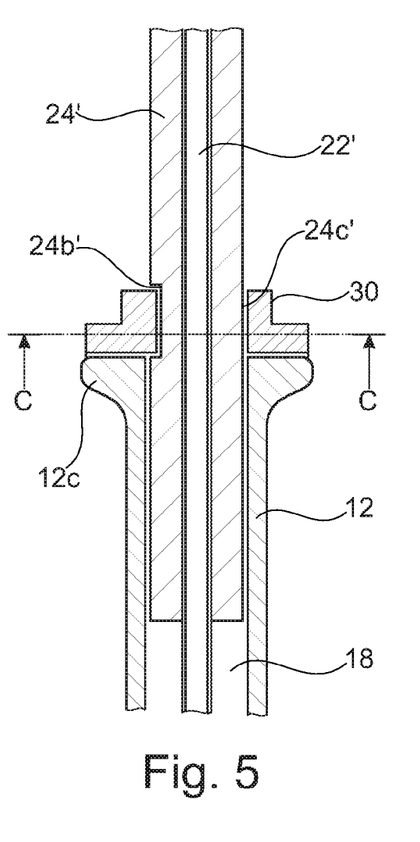
FIG. 5 shows a cross sectional view of a mechanism for limiting axial movement of the second plunger rod in accordance with an embodiment of the present invention.
Figure 6:
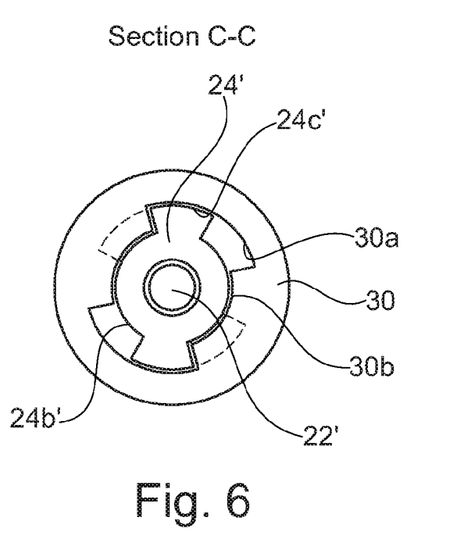
FIG. 6 shows a detailed cross sectional view of the mechanism of FIG. 5 taken along section C-C of FIG. 5.

FIG. 5 relates to an additional feature that may be present in any embodiment to limit unwanted axial movement of the second plunger rod 24. In preferable embodiments, it forms part of the syringe assembly 10' described above in relation to FIGS. 2A to 2E. As shown in FIG. 5, a collar 30 sits rearward of the flange 12c of the syringe barrel 12 and surrounds a modified second plunger rod 24' and a modified first plunger rod 22'. FIG. 6 shows a sectional view across section C-C of FIG. 5 in which it can be seen that the collar 30 is generally circular and has first inner edges 30b and second inner edges 30a that together define a central aperture. Each of the first and second inner edges 30b, 30a, has a circular profile where the notional circle of the profile of the second inner edges 30a is larger in diameter than the notional circle of the profile of the first inner edges 30b. The result is that the second inner edges 30a provide cut out portions in an otherwise circular aperture defined by the first inner edges 30b. In the embodiment shown in FIG. 6, there are two cut-out portions where each cut-out portion extends along an arc, and each cut-out portion is angularly spaced from the other cut-out portion. In alternative embodiments, other angular arrangements may be possible.

Conversely, the second plunger rod 24' has two cut-out portions each defined by an inner wall 24b'. The inner walls 24b' have a generally circular profile and the notional circle of the profile of the inner walls 24b' has a smaller diameter than an outer wall 24c' of the second plunger rod 24'. In the embodiment shown in FIG. 6, each inner wall has an angular extent and each inner wall 24b' is angularly spaced from the other inner wall 24b'. This angular arrangement corresponds to the angular arrangement of the collar 30 described above. In alternative embodiments, other angular arrangements of the collar 30 and second plunger rod 24' may be possible. In cross-section, the cut-out portions of the second plunger rod 24' define radially extending tabs therebetween.

The collar 30 provides a locking mechanism that only permits axial movement of the second plunger rod 24' in certain angular configurations of the second plunger rod 24' relative to the collar 30. In particular, axial movement of the second plunger rod 24' is permitted if the outer walls 24c' are axially aligned with the cut out portions of the collar defined by the second inner edges 30a.

In a particularly preferable embodiment, the first plunger rod 22' is initially axially moveable independent of the second plunger rod 24' so that the above-described mixing may be achieved. The second plunger rod 24' is meanwhile axially restrained by the collar 30 due to an axial misalignment of the outer walls 24c' of the second plunger rod 24' with the cut out portions of the collar defined by the second inner edges 30a. Once mixing is complete, the first plunger rod 22' may be rotated about its longitudinal axis so as to axially lock the first plunger rod 22' to the second plunger rod 24'. This may, for example, be achieved by the sleeve 23 and engagement members 23a, 23b described above. Further rotation of the first plunger rod 22' relative to the second plunger rod 24' about the longitudinal axis may cause a rotational engagement between the first plunger rod 22' and the second plunger rod 24'. This may be achieved, for example, by a splined interface between the first plunger rod 22' and the second plunger rod 24', or another angularly dependent mechanism or formation between the first plunger rod 22' and the second plunger rod 24'. Due to rotational engagement between the first plunger rod 22' and the second plunger rod 24', further rotation of the first plunger rod 22' about the longitudinal axis results in rotation of the second plunger rod 24' causing the outer walls 24c' of the second plunger rod 24' to move into axial alignment with the cut out portions of the collar 30 defined by the second inner edges 30a. In this position, axial movement of the second plunger rod 24' is possible such that axial movement of the first plunger rod 22' causes axial movement of the second plunger rod 24'.

In a preferable embodiment, a 45° rotation of the first plunger rod 22' about the longitudinal axis is required to axially lock the first plunger rod 22' to the second plunger rod 24', and a further 45° rotation of the first plunger rod 22' about the longitudinal axis is required to rotate the second plunger rod 24' (which is then rotationally engaged with the first plunger rod 22') into a rotational position where the relative axial alignment with the collar 30 permits axial movement of the second plunger rod 24'. However, in alternative embodiments, any other suitable angles may define the axial and rotational engagements between the first plunger rod 22' and the second plunger rod 24'.

In one embodiment, the assembly may be provided in a configuration where neither of the first plunger rod and second plunger rod may move axially in the barrel. A first rotation (e.g. of the first plunger rod relative to the second plunger rod) may move the assembly into a configuration where the first plunger rod may move axially relative to the second plunger rod so as to permit mixing. A second rotation (e.g. of the first plunger rod) which may or may not be in the same direction may axially lock the first plunger rod to the second plunger rod. A third rotation (e.g. a collective rotation of the first plunger rod and second plunger rod) may unlock the second plunger rod so as to permit the second plunger rod (and hence first plunger rod) to move axially and deliver a dose of medicament.

In any embodiment in accordance with the present invention, the syringe assembly 10, 10' may or may not include a needle 13. For example, another kind of applicator may be provided (or no applicator at all) for facilitating the passage of mixed medicament to the injection or delivery site. The syringe assembly of the present invention may, for example, be a nasal, ocular, oral, otic, or other medicament delivery device for delivering a dose of mixed medicament to a patient and is not limited to needle-type syringes. An applicator, for example a needle 13, may be attachable to the syringe assembly 10, 10' such that the medicaments may be mixed as a closed system, following which the applicator may be attached to the syringe assembly 10, 10' to administer the mixed medicaments to the injection site. Alternatively, a closed system may be achieved during mixing by the needle 13 or other applicator being blocked, capped or otherwise sealed. For example, the needle 13 may be initially staked in a needle boot and remain so during the mixing of the two ingredients. Then, once the ingredients are mixed to a satisfactory level, the needle boot (or other blocking, capping or sealing means) may be removed to allow the mixed ingredients to be dispensed.

Figure 7:
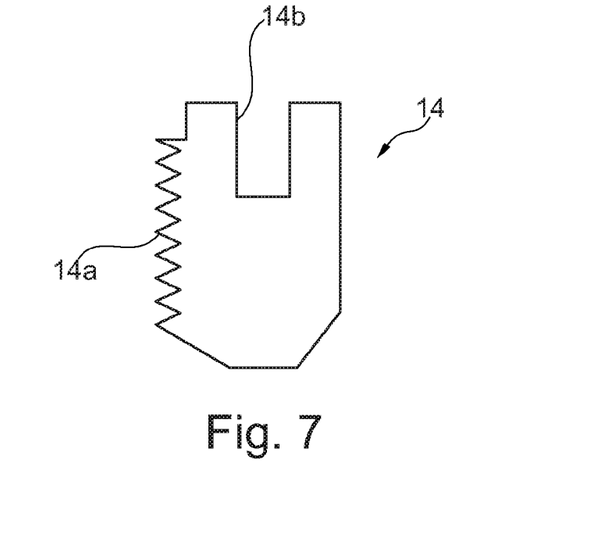
FIG. 7 shows a detailed view of the first stopper of the syringe assemblies of FIGS. 1A to 1D and FIGS. 2A to 2E.

A detailed view of the first stopper 14 is shown in FIG. 7. The first stopper 14 includes a rearward facing socket 14b for receiving and engaging with the first plunger rod 22. This may be a threaded socket or simply a recess into which the first plunger rod 22 may be affixed to the first stopper (e.g. by adhesive or friction). Indeed, the first stopper 14 may attach to the first plunger rod 22 by a friction fit or an interference fit (for example a ball and socket joint). It is important that the fit between the first stopper 14 and the first plunger rod 22 provides positive engagement therebetween in both forward and rearward axial directions to ensure that the first stopper 14 remains attached to the first plunger rod 22 during use (i.e. mixing) within the barrel 12. In one example, the first stopper 14 may only loosely engage on the first plunger rod 22 when assembled outside of the barrel 12, and the friction of the barrel 12 acting on the first stopper 14 may be used to establish a secure fit between the first stopper 14 and the first plunger rod 22 when the first stopper 14 (and first plunger rod 22') is inserted into the barrel 12. The two way valve portion 14a comprises a plurality of flexible flaps that run along one side of the first stopper 14 and create a resilient seal with the inside surface of the barrel 12. The flaps 14a deform under sufficient fluid pressure so as to permit the passage of fluids between the front and rearward sides of the first stopper 14. The resilient seal 14a may run along one side of the first stopper 14 (as shown in FIG. 7) (and have an angular extent less than 360°) or they may circumvent the entire first stopper 14 (i.e. have an angular extent of 360°), provided that they are stiff enough to prevent accidental opening, yet flexible enough to open when required. In alternative embodiments, the resilient seal 14a may be formed through the body of the first stopper 14 so that the resilient seal 14a seals against itself in the sealing configuration, rather than sealing against the barrel 12.

Figure 9:
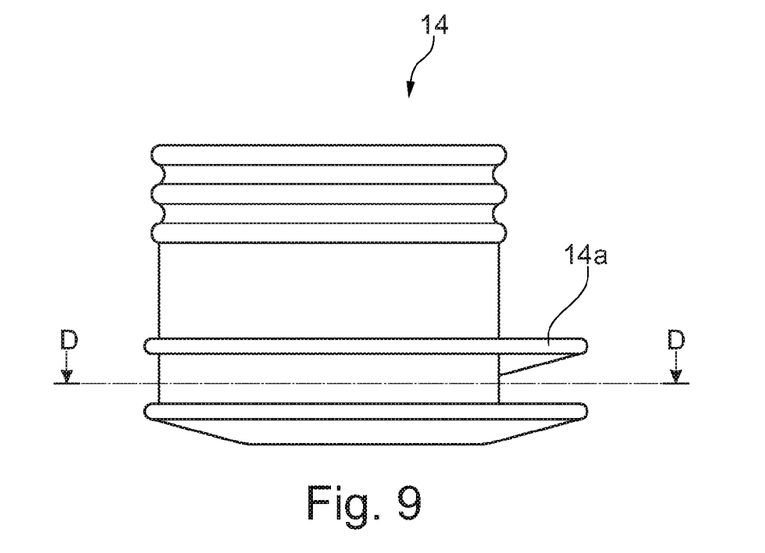
FIG. 9 shows an alternative view of a first stopper in accordance with an embodiment of the present invention.
Figure 10:
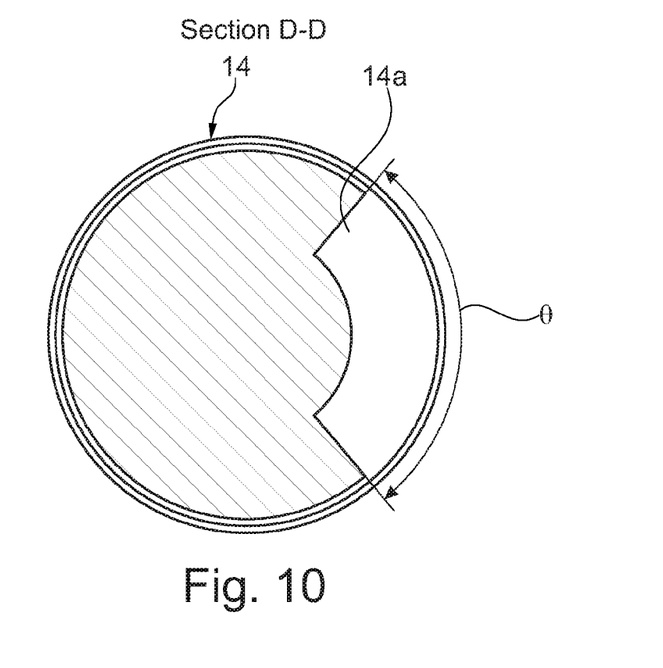
FIG. 10 shows a detailed cross sectional view of the first stopper of FIG. 9 taken along section D-D in FIG. 9.

FIG. 9 shows another view of the first stopper 14 and FIG. 10 shows a detailed view of the section D-D in FIG. 9. From FIG. 9, it can be seen that the flexible flaps 14a extend along an arc of angle $\theta$ of the circular first stopper 14. The magnitude of $\theta$ will have an effect on the rate and efficiency of missing. For example, a small $\theta$ (or otherwise small two way valve portion 14a) will, by conservation of mass, cause a rapid flow of fluid in response to axial displacement of the first stopper 14 into the volume 16, 18 containing the fluid. Optimization of this flow will optimize the mixing of the ingredients and minimize both the force and time required to achieve the desired mixing.

Figure 8:
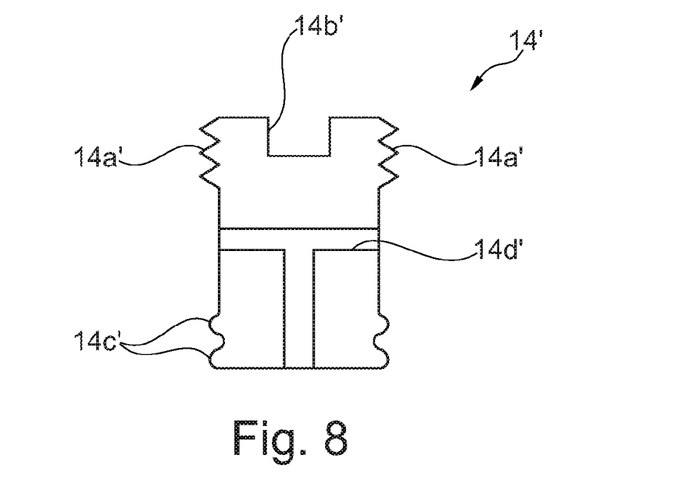
FIG. 8 shows an example of an alternative first stopper for use with a syringe assembly in accordance with an embodiment of the present invention.

An alternative embodiment of a first stopper 14' in accordance with the present invention is shown in FIG. 8. The first stopper 14' includes a rearward facing socket 14b' for receiving and engaging with the first plunger rod 22. Again, this may be a threaded socket or simply a recess into which the first plunger rod 22 may be affixed to the first stopper 14 (e.g. by adhesive or friction), or any other suitable connection means for connecting to the first plunger rod 22, as discussed above. The two way valve portion 14a' is provided by a plurality of flexible flaps that circumvent an axial section of the first stopper 14'. Additionally, the first stopper 14' includes a permanent seal 14c' that circumvents the first stopper 14' and is axially space from the flexible flaps 14a'. The permanent seal 14c' is configured to seal against the inside of the barrel 12 and does not deform sufficiently to create a fluid path across the seal. The first stopper 14' additionally includes a by-pass channel 14d' that passes from an outer side surface of the first stopper 14' axially between the flaps 14a' and the permanent seal 14c' to a front surface of the first stopper 14', thus by-passing the permanent seal 14d'. Fluid may travel along the by-pass channel 14d' such that the flaps 14a' may encounter fluid pressure from either side (front and rear) and deform putting the two way valve 14a' into the open configuration. In alternative embodiments, the flaps 14a' may not extend around the entire circumference of the first stopper 14'. In such embodiments, an additional permanent seal may make up the remainder of the circumference. Alternatively, the embodiment shown in FIG. 8 may be inverted such that the permanent seal 14c' is axially rearward of the resilient seal 14a'. In any case, the by-pass channel 14d' should by-pass the permanent seal 14c'. In by-passing the permanent seal 14c', the channel 14d' introduces a radial flow direction which provides easier control of the flow velocity of the flowing fluid.

In any embodiment, any suitable two way valve may be employed provided that it is moveable from a sealing configuration to an open configuration upon an increase in fluid pressure from either side. In any embodiment, the two way valve may be provided with a hole or other formation (e.g. a nozzle) that is configured to cause turbulence in fluid passing through the two way valve. Such an arrangement may improve mixing of the ingredients.

Although the syringe assemblies 10, 10' have been described as including two fluid ingredients, the syringe assembly 10, 10' may include a dry ingredient (e.g. a powder or lyophilized ingredient) and a wet, fluid ingredient in accordance with certain embodiments of the invention. In embodiments where a dry ingredient is present, the first stopper 14 must first move into (i.e. move axially to reduce the volume of) the volume 16, 18 containing the fluid ingredient so as to cause the first stopper 14 to move into the open configuration and permit mixing of the wet and dry ingredients. Once both volumes 16, 18 contain liquid, the first stopper 14 may be moved in either the forward or rearward axial direction as described above. The agitation provided by the moving first stopper 14 may result in an emulsion, a solution or a suspension, for example, depending on the properties of the initial separate ingredients/medicaments. Prior to use, and during assembly of the syringe assembly 10, 10', the ingredients may be introduced into the barrel 12 either side of the first stopper 14 (e.g. via the front outlet 12a and the rear open end 12b respectively) so as to prevent cross contamination.

In certain embodiments, the assembly may be provided such that only the second volume 18 contains medicament and the first volume 16 may be empty or be a substantially zero volume (in practice, however, it is likely that some small volume space will remain between the first stopper 14 and the front outlet of the barrel). In alternative embodiments, the assembly may be provided such that only the first volume 16 contains medicament and the second volume 18 may be empty or be a substantially zero volume (again, in practice, it is likely that some small volume space will remain between the first stopper 14 and the second stopper 20).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A syringe assembly comprising:
    a barrel for containing one or more medicaments, the barrel having a front outlet for allowing an expulsion of said one or more medicaments from the barrel through said front outlet;
    a first stopper disposed in the barrel and axially moveable therein and defining a first volume in the barrel axially forward of the first stopper and a second volume in the barrel axially rearward of the first stopper, the first stopper having a two way valve that is moveable between a sealing configuration and an open configuration to selectively put the first volume in fluid communication with the second volume, the two way valve being moveable from the sealing configuration to the open configuration by an increase in fluid pressure in either of the first and second volumes, and back to the sealing configuration by pressures in the first and second volumes equalizing, wherein the first stopper includes a resilient seal that deforms under a predetermined fluid pressure and further includes a permanent seal about an entire outer circumference of the first stopper that is axially spaced from the resilient seal, and a by-pass channel providing a fluidic passageway from between the resilient seal and the permanent seal around the permanent seal;
    a second stopper disposed in the barrel axially rearward of the first stopper and axially moveable therein, the second stopper providing a fluid tight seal at a rear end of the second volume;
    a first plunger rod connected to the first stopper and extending axially rearwardly through the second stopper, the second stopper sealingly engaging with the first plunger rod but permitting axial sliding of the first plunger rod therethrough wherein the first plunger rod is configured to apply the increase in fluid pressure in either the first or second volumes by axially moving the first stopper relative to the barrel; and
    a second plunger rod connected to the second stopper, so as to axially move the second stopper when the second plunger rod is axially moved;
    wherein the first plunger rod is axially moveable so as to axially move the first stopper and pressurise either of the first volume and second volume, where a pressure difference between the first volume and the second volume caused by axial movement of the first plunger by the first plunger rod causes the two way valve to move into the open configuration and fluidly connect the first volume and second volume to permit a fluid of the first volume to flow into the second volume or a fluid of the second volume to flow into the first volume; and
    wherein the two way valve is configured to permit the first stopper to repeatedly move successively axially forwardly and axially rearwardly within the barrel relative to the second stopper to encourage mixing of the fluid of the first volume and the fluid of the second volume.

2. The syringe assembly of claim 1, further comprising a removeable transit clip that is configured to prevent axial movement of the first plunger rod.

3. The syringe assembly of claim 1, wherein the first plunger rod includes one or more finger loops for facilitating handling of the first plunger rod.

4. The syringe assembly of claim 1, further comprising an engagement mechanism for engaging the first plunger rod with the second plunger rod in a predetermined position of the first plunger rod relative to the second plunger rod.

5. The syringe assembly of claim 4, wherein the engagement mechanism includes engagement members connected to the first plunger rod, the engagement members being arranged to engage with the second plunger rod when the first plunger rod is at a predetermined axial position and/or rotational position relative to the second plunger rod.

6. The syringe assembly of claim 5, wherein said engagement members project radially inwardly from a sleeve connected to the first plunger rod and surrounding the second plunger rod.

7. The syringe assembly of claim 5, wherein said engagement members are arranged to engage with a rear end of the second plunger rod by abutting said rear end of said second plunger rod.

8. The syringe assembly of claim 1, further comprising a locking mechanism for limiting axial movement of the second plunger rod.

9. The syringe assembly of claim 8, wherein axial movement of the second plunger rod is permitted when the second plunger rod is in a predetermined rotational position.

10. The syringe assembly of claim 9, wherein the locking mechanism comprises a collar and axial movement of the second plunger rod is permitted when the second plunger rod is in the predetermined rotational position relative to the collar and axial abutment between the collar and the second plunger rod prevent relative axial movement in rotational positions other than the predetermined rotational position.

11. The syringe assembly of claim 1, wherein the resilient seal includes a plurality of flexible flaps.

12. The syringe assembly of claim 1, wherein the resilient seal extends along an arc around the first stopper, wherein an angular extent of the arc is less than 360°.

13. The syringe assembly of claim 1, wherein the fluid tight seal provided by the second stopper is a sterile seal.

14. The syringe assembly of claim 1, wherein the fluid tight seal provided by the second stopper is a microbiological seal.

* * * * *